(12) United States Patent
Burbar et al.

(10) Patent No.: US 10,993,684 B1
(45) Date of Patent: May 4, 2021

(54) PET DETECTOR ASSEMBLY FOR A COMBINED PET AND CT IMAGING SYSTEM

(71) Applicant: Siemens Medical Solutions USA, Inc., Malvern, PA (US)

(72) Inventors: Ziad Burbar, Knoxville, TN (US); James L. Corbeil, Knoxville, TN (US); Jeffrey Bostrom, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 15/929,615

(22) Filed: May 13, 2020

(51) Int. Cl.
*G01T 1/29* (2006.01)
*A61B 6/00* (2006.01)
*A61B 6/03* (2006.01)

(52) U.S. Cl.
CPC ............ *A61B 6/4417* (2013.01); *A61B 6/032* (2013.01); *A61B 6/037* (2013.01); *G01T 1/2985* (2013.01)

(58) Field of Classification Search
CPC ....... A61B 6/4417; A61B 6/032; A61B 6/037; A61B 6/4258; A61B 6/4266; G01T 1/2985; G01T 1/164
See application file for complete search history.

(56) References Cited

U.S. PATENT DOCUMENTS

| | | | | |
|---|---|---|---|---|
| 5,391,877 A * | 2/1995 | Marks | ............. | A61B 6/032 250/363.03 |
| 6,205,347 B1 * | 3/2001 | Morgan | ............. | A61B 6/04 600/407 |
| 6,303,935 B1 * | 10/2001 | Engdahl | ............. | G01T 1/1648 250/363.03 |
| 6,490,476 B1 * | 12/2002 | Townsend | ............. | A61B 6/032 250/363.03 |
| 6,700,949 B2 * | 3/2004 | Susami | ............. | A61B 6/4417 250/363.03 |
| 6,810,103 B1 * | 10/2004 | Tybinkowski | ............. | A61B 6/032 250/363.04 |
| 6,831,961 B1 * | 12/2004 | Tybinkowski | ............. | A61B 6/032 250/363.04 |
| 6,878,941 B2 * | 4/2005 | Balan | ............. | A61B 6/4429 250/363.02 |
| 6,920,196 B2 * | 7/2005 | Ueno | ............. | A61B 6/032 250/363.03 |
| 6,965,661 B2 * | 11/2005 | Kojima | ............. | G01T 1/1648 378/10 |
| 7,154,096 B2 * | 12/2006 | Amano | ............. | A61B 6/032 250/363.03 |
| 7,297,958 B2 * | 11/2007 | Kojima | ............. | A61B 6/4241 250/363.03 |
| 7,374,337 B2 * | 5/2008 | Yunker | ............. | A61B 6/00 250/363.02 |
| 7,412,027 B2 * | 8/2008 | Yakubovsky | ............. | A61B 6/04 378/195 |
| 8,260,013 B2 * | 9/2012 | Pekar | ............. | G06T 7/33 382/128 |

(Continued)

*Primary Examiner* — David P Porta
*Assistant Examiner* — Djura Malevic

(57) ABSTRACT

Disclosed is a PET detector assembly in a combined PET/CT scanner system having a backplane structure for supporting two or more PET detector rings that provides substantially balanced load on the gantry backplane while accommodating the varying number of PET detector rings between short axial PET FOV system as well as long axial PET FOV system.

12 Claims, 6 Drawing Sheets

(56) References Cited

U.S. PATENT DOCUMENTS

| | | | | |
|---|---|---|---|---|
| 8,344,326 B2* | 1/2013 | Amano | G01T 1/2985 | 250/363.03 |
| 8,581,196 B2* | 11/2013 | Yamaya | A61N 5/1048 | 250/363.03 |
| 8,594,404 B2* | 11/2013 | Yamaya | G01T 1/2985 | 382/131 |
| 8,630,696 B2* | 1/2014 | Kim | A61B 6/5235 | 600/427 |
| 9,014,330 B2* | 4/2015 | Takayama | A61B 6/54 | 378/19 |
| 9,029,787 B2* | 5/2015 | Yamaya | G01T 1/1603 | 250/363.03 |
| 9,121,893 B2* | 9/2015 | Schmand | G01R 33/381 | |
| 9,316,743 B2* | 4/2016 | Rousso | G01T 1/1647 | |
| 9,606,199 B2* | 3/2017 | Breuer | G01R 33/481 | |
| 9,880,236 B2* | 1/2018 | Obata | A61B 6/037 | |
| 9,947,116 B2* | 4/2018 | Matthews | G06T 11/006 | |
| 10,036,790 B2* | 7/2018 | Schmand | G01T 1/1603 | |
| 10,413,267 B2* | 9/2019 | Gagnon | G01N 23/046 | |
| 10,912,528 B2* | 2/2021 | Corbeil | A61B 6/037 | |
| 2002/0090050 A1* | 7/2002 | Nutt | G01T 1/1648 | 378/19 |
| 2003/0012331 A1* | 1/2003 | Kojima | G01T 1/1615 | 378/4 |
| 2003/0058984 A1* | 3/2003 | Susami | A61B 6/037 | 378/19 |
| 2003/0076925 A1* | 4/2003 | DeSilets | A61B 8/5238 | 378/63 |
| 2003/0118155 A1* | 6/2003 | Ueno | G01T 1/1644 | 378/177 |
| 2003/0179853 A1* | 9/2003 | Amemiya | G01T 1/1648 | 378/63 |
| 2004/0097800 A1* | 5/2004 | Crosetto | G01T 1/2985 | 600/407 |
| 2005/0067577 A1 | 3/2005 | Yanagita et al. | | |
| 2005/0067578 A1 | 3/2005 | Veno et al. | | |
| 2005/0109943 A1* | 5/2005 | Vaquero | G01T 1/1644 | 250/363.04 |
| 2007/0080295 A1* | 4/2007 | Hamill | G01T 1/2985 | 250/363.03 |
| 2007/0102641 A1* | 5/2007 | Schmand | G01R 33/381 | 250/363.03 |
| 2008/0146914 A1* | 6/2008 | Polzin | A61B 5/055 | 600/420 |
| 2009/0108206 A1* | 4/2009 | Breuer | G01R 33/28 | 250/363.03 |
| 2009/0154647 A1* | 6/2009 | Matsuzawa | A61B 6/04 | 378/98 |
| 2009/0159804 A1* | 6/2009 | Shibuya | G01T 1/2985 | 250/363.03 |
| 2009/0226066 A1* | 9/2009 | Williams | A61B 6/037 | 382/131 |
| 2009/0264753 A1* | 10/2009 | von Schulthess | A61B 6/037 | 600/431 |
| 2010/0040197 A1* | 2/2010 | Maniawski | A61B 6/037 | 378/65 |
| 2010/0046821 A1* | 2/2010 | Manjeshwar | G06T 11/008 | 382/131 |
| 2010/0128956 A1* | 5/2010 | Yamaya | G01T 1/2985 | 382/132 |
| 2010/0183213 A1* | 7/2010 | Keppel | A61B 6/502 | 382/131 |
| 2011/0077511 A1* | 3/2011 | Kim | A61B 6/037 | 600/427 |
| 2011/0288407 A1* | 11/2011 | Brinks | A61B 6/037 | 600/427 |
| 2012/0046544 A1* | 2/2012 | Inoue | A61B 6/5235 | 600/425 |
| 2012/0112078 A1* | 5/2012 | Millett | G01T 1/2985 | 250/363.03 |
| 2012/0161014 A1* | 6/2012 | Yamaya | A61B 6/037 | 250/363.03 |
| 2013/0322717 A1* | 12/2013 | Bar-Shalev | G06T 7/74 | 382/131 |
| 2014/0249408 A1* | 9/2014 | Collins | A61B 6/037 | 600/427 |
| 2014/0334702 A1* | 11/2014 | El Fakhri | G06T 11/005 | 382/131 |
| 2015/0073272 A1* | 3/2015 | Corbeil | A61B 6/4417 | 600/427 |
| 2015/0369890 A1* | 12/2015 | Schmand | G01R 33/26 | 324/322 |
| 2016/0183890 A1* | 6/2016 | Nathan | A61B 6/4417 | 378/9 |
| 2016/0183893 A1* | 6/2016 | Zhang | A61B 6/4476 | 250/363.05 |
| 2016/0209514 A1* | 7/2016 | Moskal | A61B 6/037 | |
| 2017/0311919 A1* | 11/2017 | Gagnon | A61B 6/032 | |

* cited by examiner

PET DETECTOR ASSEMBLY FOR A COMBINED PET AND CT IMAGING SYSTEM

FIELD

This specification relates to combined positron emission tomography (PET) and computed tomography (CT) imaging systems and, more particularly, to a PET detector assembly wherein at least one PET detector is located on each side of a neutral axis of a backplane of the PET scanner.

BACKGROUND

In medical imaging, a computed tomography (CT) scanning modality can be used to provide images of the internal structures of a human body, such as the bones. In addition, a positron emission tomography (PET) scanning modality can be used to provide images of the functional aspects of the body, usually corresponding to the metabolic uptake of an internal organ or tissue. It is frequently desirable to combine the CT and PET modalities to provide a co-registered image or series of images to assist in non-invasively studying physiological processes and structures within the body.

In a CT scan, an x-ray source is passed around a patient. Detectors around the patient then respond to an x-ray transmission through the patient to produce an image of the area of study. In a PET scan, a short-lived radioisotope is injected into a patient. For example, one such radioisotope is fluorodeoxyglucose (FDG). During the PET scan, the patient is positioned in a tunnel within a PET scanner gantry. The radioisotope undergoes positron emission decay and emits a positron. The positron encounters and annihilates with an electron to produce a pair of gamma rays moving in approximately opposite directions. The gamma rays are then detected by a plurality of PET detectors (a.k.a. gamma detectors) arranged around the circumference of the tunnel.

A representative layout of a combined PET/CT scanner system 500 is shown in FIG. 1. The PET/CT scanner system 500 includes a PET scanner portion 510, a CT scanner portion 520, and a patient bed 530. One metric of such PET/CT scanner system's capability is its ability to acquire serial images, in which, field-of-view (FOV) of both modalities are maximized. The extended stroke of the patient bed 530 defines the FOV of the CT scanner 520. The PET FOV, however, because it is positioned farther from the patient bed 530, inherently has a FOV scan that is much shorter than that of the CT scanner 520. The co-scan, the effective overlapping scan area of the combined modalities PET and CT, is largely dependent on three parameters: (1) the extension length of the patient bed 530; (2) the FOV separation distance 550 as taken from the center C1 of the CT FOV and the first plane P1 of the PET FOV; and (3) the axial length 560 of the PET FOV.

The spatial arrangement of the three components introduces a couple of challenges to the system design. In certain CT embodiments, the CT FOV is shifted to the patient side of the CT scanner 520, assisting in interventional therapy. This accommodation increases the separation between the CT scanner 520 and the PET scanner 510, thus increasing the FOV separation distance 550.

Another challenge arises most often in newer PET/CT scanner system designs where a common PET gantry is tasked with structurally supporting both the short and long PET FOV axial length 560 designs.

In a conventional PET detector assembly 10 used in PET/CT scanner systems shown in FIG. 2, the rings 20 of PET detectors 12 are mounted on and supported by a gantry backplane 14. Generally, a PET modality includes more than one detector rings but in FIG. 2, only one PET detector ring 20 is shown. The PET detector ring(s) 20 are all mounted on one side of the gantry backplane 14. For the purposes of discussion, a neutral or vertical plane 16 of the gantry backplane 14 is defined and identified as the center of the gantry backplane 14 in the axial direction of the PET/CT scanner when viewed from the side as shown in FIG. 1. Because all of the PET detector ring(s) 20 are mounted on one side of the gantry backplane 14, the PET detector rings 20 are on one side of the neutral vertical plane 16. The PET detectors 12 are configured such that they extend from a face 18 of the backplane 14 in a cantilevered arrangement. The center of mass of such cantilevered PET detector ring 20 is positioned to one side of the neutral vertical plane 16 of the gantry backplane 14. This results in a moment load W being on one side of the neutral vertical plane 16 as noted in FIG. 1. Therefore, when the PET/CT scanner system design calls for a long PET FOV axial length 560, that requires more number of PET detector rings to cover the longer PET FOV axial length. This also produces a greater moment load W on the gantry backplane 14. In turn, that requires more structurally robust gantry backplane 14 which increases the cost of the PET/CT scanner system.

In the conventional PET/CT scanner systems, the FOV separation distance 550 in a system is kept constant for design simplicity regardless of the axial length 560 of the PET FOV, for example, between a 3-ring PET detector system and a 4-ring PET detector system. This compromise was acceptable in the past because the difference in the PET FOV axial length 560 was on the order of 4-6 cm. With the advent of more modern PET/CT scanner systems, however, the trend has been toward longer PET FOV axial lengths, on the order of 16-40 cm, which requires many more cantilevered PET detector rings being mounted on the gantry backplane 14 with greater moment load W.

Therefore, there is a need for an improved PET/CT scanner system's PET detector assembly.

SUMMARY

According to an aspect of the present disclosure, a PET detector assembly in a combined PET/CT scanner system comprises a backplane structure for supporting two or more PET detector rings; two or more PET detector rings that are mounted on the backplane, wherein the two or more PET detector rings define a PET detector field of view (FOV); and a CT scanner defining a CT FOV; where the backplane defines a neutral vertical plane; where when there are an even number of PET detector rings, half of the PET detector rings are at least partially disposed on a first side of the neutral vertical plane such that, the half of the PET detector rings are at least partially between the neutral vertical plane and the CT FOV and the remaining half of the PET detector rings are at least partially disposed on a second side of the neutral vertical plane that is opposite the first side; and where when there are an odd number $X_{odd}$ of PET detector rings, the side of the neutral vertical plane that is nearer the CT FOV has $n=(X_{odd}+1)/2$ number of PET detector rings at least partially disposed on a first side of the neutral vertical plane such that, the n number of PET detector rings are at least partially between the neutral vertical plane and the CT FOV and n−1 number of PET detector rings are at least partially disposed on a second side of the neutral vertical plane that is opposite the first side.

A combined PET/CT scanner system incorporating a PET detector assembly of the present disclosure is also provided.

BRIEF DESCRIPTION OF DRAWINGS

The features of the embodiments described herein will be more fully disclosed in the following detailed description, which is to be considered together with the accompanying drawings wherein like numbers refer to like parts. All illustrations are schematic and they are not intended to show actual dimensions or proportions.

DETAILED DESCRIPTION

Figure 1:
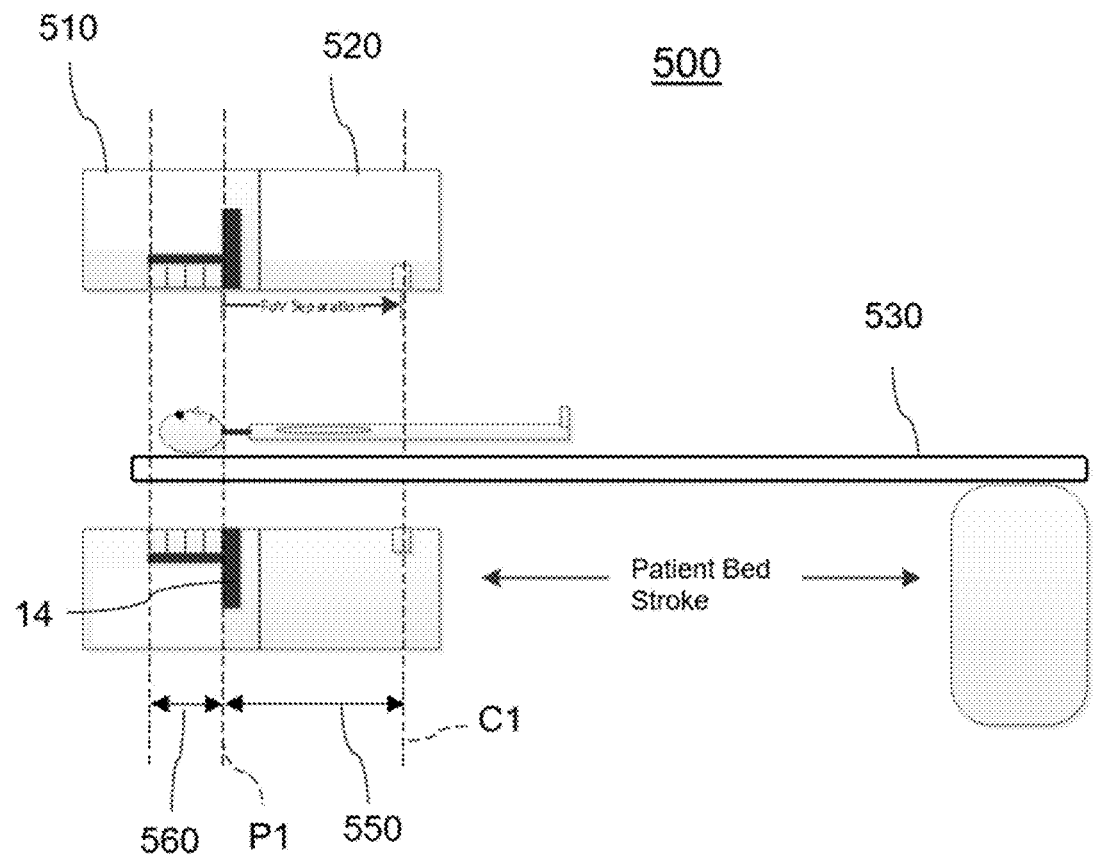
FIG. 1 is a representative layout of a combined PET/CT scanner system.
Figure 2:
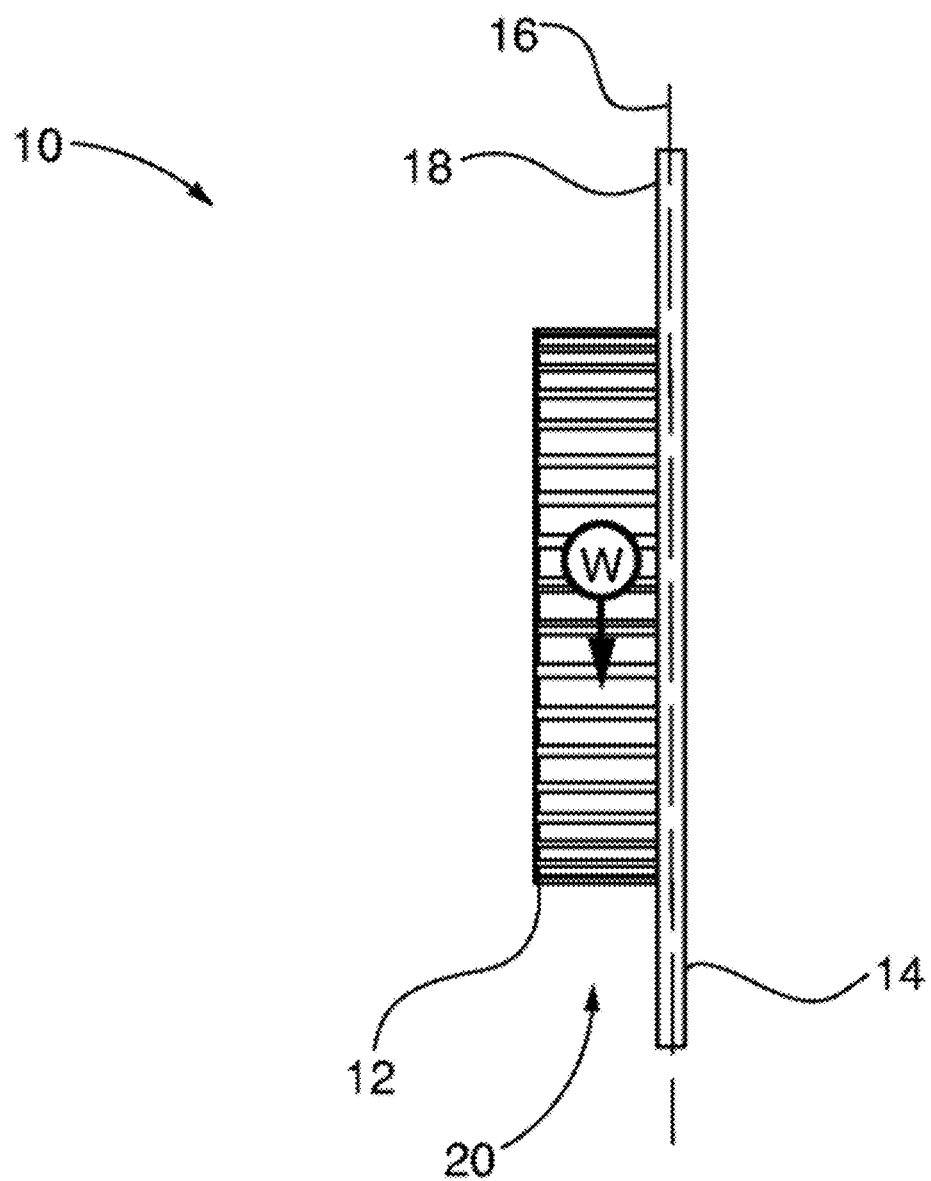
FIG. 2 is an illustration of a side view of a conventional assembly for cantilevered PET detectors arranged on a gantry backplane.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

The present disclosure describes combined PET and CT imaging systems in which PET detectors are positioned on each side of the backplane, or supporting structure, of the PET scanner. Arranging the PET detectors in this way reduces the cantilever load on the backplane, which may allow the backplane to include less material. The more balanced arrangement of the PET detectors described herein may also allow for easier access for servicing of the PET detectors. Further, the separation of the field of view (FOV) of the PET and CT imagers may be held constant while changing the FOV of the PET imager.

Figure 3:
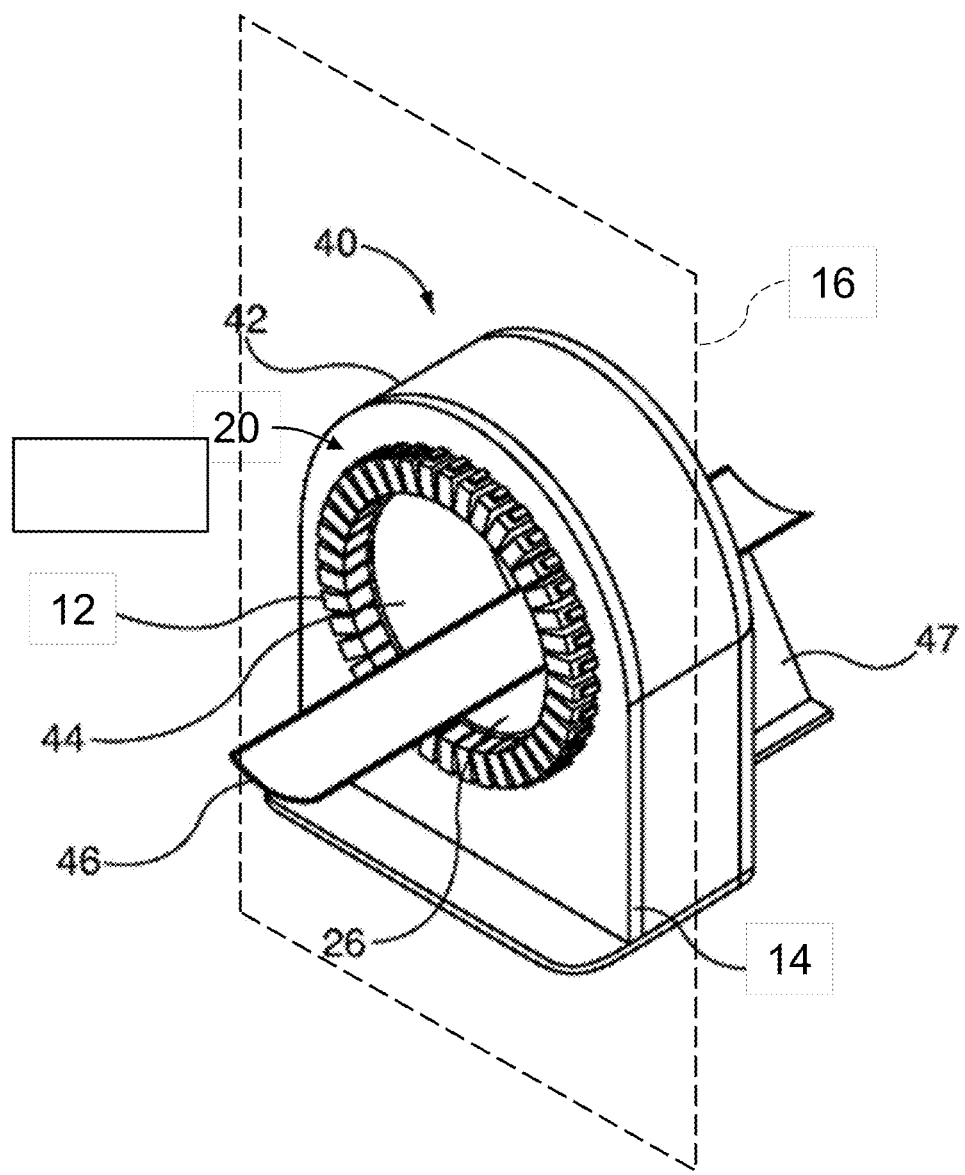
FIG. 3 is a partial view of a PET and CT imaging system which depicts a backplane and PET, according to one embodiment described herein.

Referring to FIG. 3, a partial view of a combined PET/CT scanner system 40 is shown which depicts a backplane 14 and a ring 20 PET detectors 12. The PET/CT scanner system 40 includes an enclosure 42 having a patient tunnel 44 and a bed 46 for holding a patient. The bed 46 is supported by a bed traversing mechanism 47 that serves to move the bed 46 and, thus, the patient relative to the patient tunnel 44 during scanning. In other embodiments, the bed 46 is stationary and the combined PET/CT scanner system 40 moves relative to the bed 46. The combined PET/CT scanner system 40 utilizes known PET and CT scanning techniques and associated components to generate PET and CT scans of the patient either sequentially or simultaneously without requiring the patient to get off the bed 46.

Figure 4:
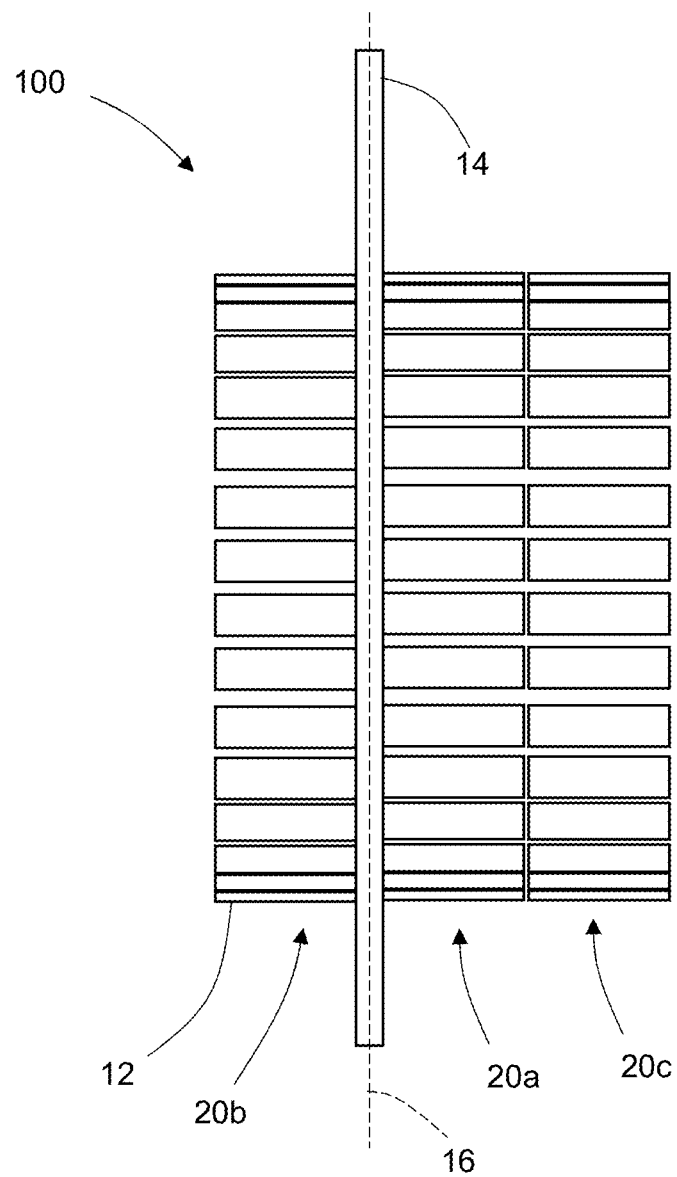
FIG. 4 is a schematic illustration of a PET detector assembly for a PET scanner, according to embodiments described herein.
Figure 5:
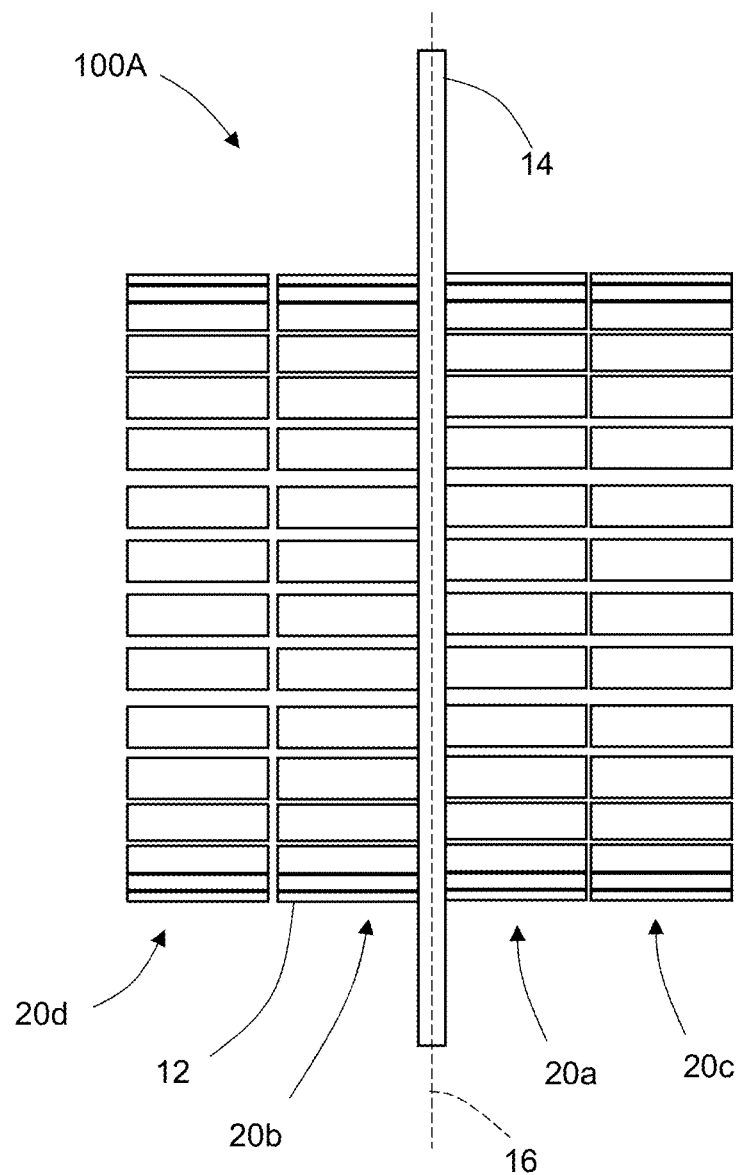
FIG. 5 is a schematic illustration of a PET detector assembly for a PET scanner, according to another embodiment described herein.

Referring to FIGS. 4 and 5, schematic illustrations of an embodiment of a PET detector assembly 100 and another embodiment of a PET detector assembly 100A for a PET scanner portion of the combined PET/CT scanner system 40 are shown. The PET detector assembly 100 shown in FIG. 4 includes a series of rings 20a, 20b, 20c of detectors 12, with each detector 12 supported by the backplane 14. The PET detector assembly 100A shown in FIG. 5 includes a series of rings 20a, 20b, 20c, 20d of detectors 12, with each PET detector 12 supported by the backplane 14. The backplane 14 is configured to be mounted to the ground or an intervening structure to support the detectors 12. The backplane 14 has a circular aperture that forms part of the patient tunnel 44 of the combined PET/CT scanner system 40 (shown in FIG. 3). The PET detectors 12 are circumferentially arranged on the backplane 14 about the patient tunnel 44.

In both embodiments of the PET detector assemblies 100 and 100A, at least one of the rings 20a, 20b, 20c, 20d of PET detectors 12 is positioned on either side of the neutral vertical plane 16 of the backplane 14. For example, in the illustrated example of FIG. 4, two detector rings 20a, 20c are positioned on a first side of the neutral vertical plane 16 of the backplane 14 (e.g., closer to the CT portion of the PET/CT scanner system 40) and a detector ring 20b is positioned on the opposite side of the neutral vertical plane 16 (e.g., farther from the CT portion of the PET/CT scanner system 40). In the illustrated example of FIG. 5, two detector rings 20a, 20c are positioned on a first side of the neutral vertical plane 16 of the backplane 14 (e.g. closer to the CT portion of the PET/CT scanner system 40) and two detector rings 20b, 20d are positioned on the opposite side of the neutral vertical plane 16 (e.g., farther from the CT portion of the PET/CT scanner system 40).

Positioning at least one ring of PET detectors 12 on each side of the backplane 14 reduces the moment load on the backplane 14 caused by the PET detectors 12. As a result, stresses on the backplane 14 are reduced, thus reducing the structural strength and/or stiffness requirement for the backplane 14. This provides additional design flexibility and material choices for fabricating the backplane 14 and also can reduce the cost of the materials. For example, the backplane 14 can be fabricated from relatively inexpensive foam or cardboard material sandwiched between sheets of aluminum, thus reducing fabrication costs.

In addition, this arrangement of the PET detectors 12 enables fabrication of a lighter backplane 14 resulting in reduced transportation and installation costs. Further, this arrangement of the PET detectors 12 reduces the risk that vibration induced damage to the PET/CT scanner system.

The PET detector assembly 100 can comprise any number of PET detector rings odd or an even number. For example, the PET detector assembly 100 can include three PET detector rings 20a, 20b, 20c (as shown in FIG. 4), four PET detector rings 20a, 20b, 20c, 20d (as shown in FIG. 5), etc.

In applications in which the PET detector assembly 100A includes an even number of PET detector rings, same number of PET detector rings can be positioned on either side of the neutral vertical plane 16 defined by the backplane 14. For example, as shown in FIG. 5, in applications in which the PET/CT scanner system 40 includes four rings 20a, 20b, 20c, 20d of PET detectors 12, two rings 20a, 20c are positioned on the side of the neutral vertical plane 16 that is nearer the CT scanner and rings 20b, 20d are positioned on the opposite side of the neutral vertical plane 16 that is farther from the CT scanner.

Thus, according to the present disclosure, to reduce the moment load on the backplane 14 caused by the PET detectors 12, the PET detector assembly is to be designed so that (1) when the total number of PET detector rings in the PET/CT scanner system is an even number, equal number of PET detector rings are on either side of the neutral vertical plane 16 of the backplane 14, and (2) when the total number of PET detector rings in the PET/CT scanner system is an odd number, the side of the neutral vertical plane 16 that is nearer the CT scanner has n number of PET detector rings and the opposite side of the neutral vertical plane 16 (i.e., the side farther from the CT scanner) has n−1 number of PET detector rings where n+(n−1)=the total number of PET detector rings. Thus, if the total number of PET detector rings in the PET/CT scanner system is an even number Xeven, the PET detector assembly would comprise Xeven/2 number of PET detector rings on either side of the neutral vertical plane 16 of the gantry backplane 14. If the total number of PET detector rings in the PET/CT scanner system is an odd number Xodd, the PET detector assembly would comprise n=(Xodd+1)/2 number of PET detector rings on the side of the neutral vertical plane 16 and n−1 number of PET detector rings on the opposite side of the neutral vertical plane 16. Thus, one side of the neutral vertical plane 16 will have one more PET detector ring than the other side. It does not matter, however, which side (i.e., the side farther from the CT scanner or the side closer to the CT scanner) ends up with one more PET detector ring.

An advantage of the PET detector assembly 100, 100A disclosed herein is that the distance from the CT FOV to the nearest PET detector ring's FOV (the axial FOV separation distance 550 between PET and CT) is the same for an assembly with three PET detector rings (shown in FIG. 4) and an assembly with four PET detector rings (shown in FIG. 5). This is also true for assemblies of five PET detector rings and six PET detector rings, as well as for assemblies of seven PET detector rings and eight PET detector rings. This makes it simpler to design the system level software that determines the patient bed stroke distance between the PET FOV and the CT FOV because every two PET detector assemblies have the same distance between the PET FOV and the CT FOV. This is further illustrated in Table 1 and described below. The specific arrangement of the PET detector rings can be provided to the system level software such that the software can calculate the proper patient bed stroke.

Table 1 provides exemplary arrangements for rings of PET detectors according to embodiments described herein. Table 1 shows exemplary arrangements for a PET/CT scanner system having a co-scan length of 200 cm. Given that co-scan range, the maximum FOV separation between the PET scanner and the CT scanner is provided for a given number of rings of detectors. As shown in Table 1, in order to maintain the desired co-scan range, the maximum allowed FOV separation is reduced as more rings of PET detectors are added to the PET scanner. This is because the axial FOV of the PET scanner increases with the addition of each ring of detectors.

TABLE 1

| # of Rings of Detectors | Axial FOV of PET Scanner | Maximum Required FOV Separation | Design FOV Separation |
|---|---|---|---|
| 3 | 176 mm | 530 mm | 517 mm |
| 4 | 236 mm | 517 mm | |
| 5 | 296 mm | 503 mm | 490 mm |
| 6 | 356 mm | 490 mm | |
| 7 | 416 mm | 477 mm | 464 mm |
| 8 | 476 mm | 464 mm | |

Figure 6:
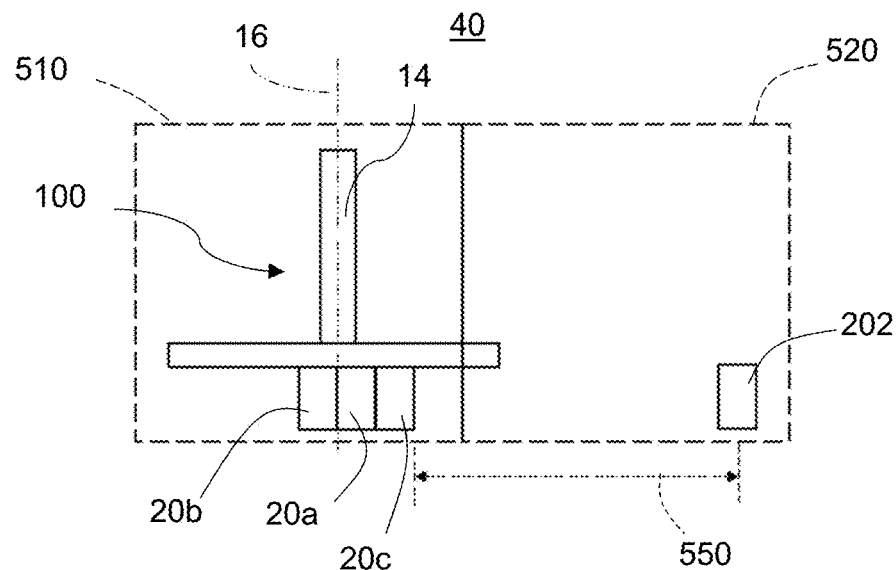
FIGS. 6 and 7 are schematic illustrations of portions of a PET detector and CT imaging system depicting the separation of the FOV of the PET and CT scanners.
Figure 7:
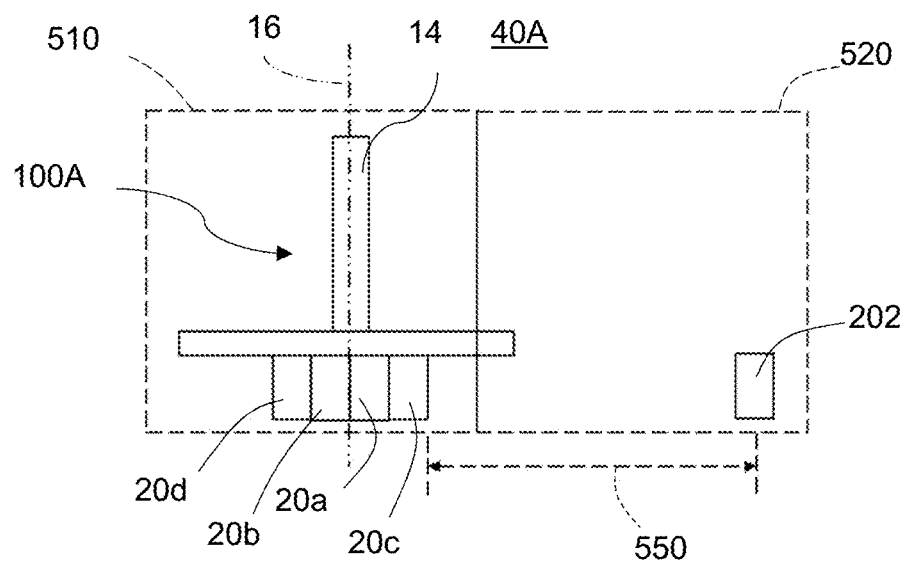

FIGS. 6 and 7 show schematic illustrations of the PET/CT scanner systems 40 and 40A, respectively. Each PET/CT scanner comprises a PET scanner portion 510 and a CT scanner portion 520. The CT scanner portion 520 has a CT FOV 202. The PET/CT scanner system 40 shown in FIG. 6 has a PET detector assembly 100 comprising three PET detector rings 20a-20c, defining the PET FOV, that are mounted on a gantry backplane 14 defining a neutral vertical plane 16. The PET/CT scanner system 40A shown in FIG. 7 comprises four PET detector rings 20a-20d, defining the PET FOV, that are mounted on a gantry backplane 14 defining a neutral vertical plane 16. As shown in FIGS. 6 and 7, each PET/CT scanner system 40, 40A has the same axial FOV separation 550. This is also shown in Table 1, wherein for a co-scan region of 200 cm, an imaging system in which the PET scanner has three or four rings of PET detectors has an axial FOV separation of 517 mm. Similarly, as shown in Table 1, an imaging system in which the PET scanner has five or six rings of detectors has an axial FOV separation of 490 mm. The five-ring assembly results from adding an additional PET detector ring next to ring 20c on the side of the neutral vertical plane 16 that is nearer to the CT scanner 520. The six-ring assembly results from adding another PET detector ring next to ring 20d on the other side of the neutral vertical plane 16 that is opposite from the side of the ring 20c. Further, as shown in Table 1, an imaging system in which the PET scanner has seven or eight rings of detectors has an axial FOV separation of 464 mm. The seven-ring assembly results from adding an additional PET detector ring next to the fifth PET detector ring on the side of the neutral vertical plane 16 that is nearer to the CT scanner 520. The eight-ring assembly results from adding another PET detector ring next to the sixth PET detector ring on the other side of the neutral vertical plane 16 that is opposite from the side of the ring 20c.

The PET detector assembly 100, 100A disclosed herein provides a balanced PET scanner gantry where the PET detectors span a gantry support backplane, represents the most efficient use of the space in the gantry, yielding the most compact design, and the axial length of the detectors alone drive the overall gantry width. Some of the benefits of the PET detector assembly of the present disclosure are: a balanced PET system for the range of the axial PET FOV lengths; achieving the required co-scan range without changing the patient bed and without adding system footprint; reduction in weight and cost of a balanced over a cantilevered gantry, as there is little to no moment to support; and ease of service access to the PET detectors without opening the gantry. To service the PET detectors, the gantry cover needs to be removed to access the PET detectors. However, in the PET/CT scanner system of the present disclosure, the PET detector assembly 100, 100A and the CT scanner 520 do not need to be separated to access the PET detectors.

In various embodiments, the PET detectors 12 can be of the type known as time-of-flight (TOF) detectors. A TOF detector has enhanced sensitivity due to the better positioning (through better electronic timing) of events along a line of coincidence. Alternatively, non-TOF types of detectors may be used. Further, the PET detectors 12 may include photo sensors such as photomultiplier tubes (PMTs), avalanche photo diodes (APDs) and/or silicon photo multipliers (SiPMs). It should be understood that these are only some examples of PET detectors and that other types of detectors may be used.

It will be understood that the foregoing description is of exemplary embodiments of this invention, and that the invention is not limited to the specific forms shown. Modifications may be made in the design and arrangement of the elements without departing from the scope of the invention.

What is claimed is:

1. A PET detector assembly in a combined positron emission tomography (PET)/computed tomography (CT) scanner system, the PET detector assembly comprising: a backplane structure for supporting two or more PET detector rings; two or more PET detector rings that are mounted on the backplane, wherein the two or more PET detector rings define a PET detector field of view (FOV); and a CT scanner defining a CT FOV;

wherein the backplane defines a neutral vertical plane; wherein when there are an even number of PET detector rings, half of the PET detector rings are at least partially disposed on a first side of the neutral vertical plane such that, the half of the PET detector rings are at least partially between the neutral vertical plane and the CT FOV and the remaining half of the PET detector rings are at least partially disposed on a second side of the neutral vertical plane that is opposite the first side; and wherein when there are an odd number Xodd of PET detector rings, one of the first and second sides of the neutral vertical plane has n=(Xodd+1)/2 number of PET detector rings at least partially disposed on that side of the neutral vertical plane and n−1 number of PET detector rings are at least partially disposed on the other of the first and second sides of the neutral vertical plane.

2. The PET detector assembly of claim 1, wherein the backplane partially defines a tunnel for receiving a patient bed.

3. The PET detector assembly of claim 1, wherein the PET detectors are time-of-flight (TOF) detectors.

4. The PET detector assembly of claim 1, wherein the PET detectors include photomultiplier tubes (PMTs).

5. The PET detector assembly of claim 1, wherein the PET detectors include avalanche photo diodes (APDs).

6. The PET detector assembly of claim 1, wherein the PET detectors include silicon photo multipliers (SiPMs).

7. A combined positron emission tomography (PET)/computed tomography (CT) scanner system comprising: a PET detector assembly comprising: a backplane structure for supporting two or more PET detector rings; two or more PET detector rings that are mounted on the backplane, wherein the two or more PET detector rings define a PET detector field of view (FOV); and a CT scanner defining a CT FOV; wherein the backplane defines a neutral vertical plane; wherein when there are an even number of PET detector rings, half of the PET detector rings are at least partially disposed on a first side of the neutral vertical plane such that, the half of the PET detector rings are at least partially between the neutral vertical plane and the CT FOV and the remaining half of the PET detector rings are at least partially disposed on a second side of the neutral vertical plane that is opposite the first side; and wherein when there are an odd number Xodd of PET detector rings, one of the first and second sides of the neutral vertical plane has n=(Xodd+1)/2 number of PET detector rings at least partially disposed on that side of the neutral vertical plane and n−1 number of PET detector rings are at least partially disposed on the other of the first and second sides of the neutral vertical plane.

8. The combined PET/CT scanner system of claim 7, wherein the backplane partially defines a tunnel for receiving a patient bed.

9. The combined PET/CT scanner system of claim 8, wherein the PET detectors are time-of-flight (TOF) detectors.

10. The combined PET/CT scanner system of claim 8, wherein the PET detectors include photomultiplier tubes (PMTs).

11. The combined PET/CT scanner system of claim 8, wherein the PET detectors include avalanche photo diodes (APDs).

12. The combined PET/CT scanner system of claim 8, wherein the PET detectors include silicon photo multipliers (SiPMs).

* * * * *